(12) United States Patent
Lamego et al.

(10) Patent No.: US 9,445,759 B1
(45) Date of Patent: Sep. 20, 2016

(54) BLOOD GLUCOSE CALIBRATION SYSTEM

(71) Applicant: Cercacor Laboratories, Inc., Irvine, CA (US)

(72) Inventors: Marcelo M. Lamego, Cupertino, CA (US); Massi Joe E. Kiani, Laguna Niguel, CA (US); Jesse Chen, Foothill Ranch, CA (US); Mathew Paul, Irvine, CA (US); Hoi Wong, Lake Forest, CA (US)

(73) Assignee: CERCACOR LABORATORIES, INC., Irvine, CA (US)

( * ) Notice: Subject to any disclaimer, the term of this patent is extended or adjusted under 35 U.S.C. 154(b) by 791 days.

(21) Appl. No.: 13/726,539

(22) Filed: Dec. 24, 2012

Related U.S. Application Data

(60) Provisional application No. 61/579,460, filed on Dec. 22, 2011.

(51) Int. Cl.
| | | |
|---|---|---|
| *A61B 5/1455* | (2006.01) | |
| *A61B 5/1495* | (2006.01) | |
| *A61B 5/0205* | (2006.01) | |
| *A61B 5/026* | (2006.01) | |
| *A61B 5/145* | (2006.01) | |
| *A61B 5/15* | (2006.01) | |

(52) U.S. Cl.
CPC ........... *A61B 5/1495* (2013.01); *A61B 5/0205* (2013.01); *A61B 5/0261* (2013.01); *A61B 5/1455* (2013.01); *A61B 5/14532* (2013.01); *A61B 5/150358* (2013.01)

(58) Field of Classification Search
CPC ... A61B 5/1455; A61B 5/14532; A61B 5/72
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |

(Continued)

OTHER PUBLICATIONS

US 8,845,543, 09/2014, Diab et al. (withdrawn)

*Primary Examiner* — Eric Winakur
(74) *Attorney, Agent, or Firm* — Knobbe Martens Olson & Bear, LLP

(57) ABSTRACT

A blood glucose calibration system has a noninvasive sensor that attaches to a person's tissue site so as to generate multi-stream physiological data responsive to that person's blood constituents. Composite parameters, each in the form of a mathematical combination of invasive blood panel parameters, are derived from a general population and are responsive to the multi-stream physiological data. A population-based, blood glucose estimate for that person is derived from a weighted and scaled combination of these composite parameters. An individualized blood glucose estimate is then derived from the population-based blood glucose estimate and intermittent invasive test strip measurements of that particular individual.

16 Claims, 9 Drawing Sheets

(56) References Cited

U.S. PATENT DOCUMENTS

| | | | |
|---|---|---|---|
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,507,288 A * | 4/1996 | Bocker ............ A61B 5/14532 600/322 |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |

(56) References Cited

U.S. PATENT DOCUMENTS

| | | |
|---|---|---|
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |

(56) References Cited

U.S. PATENT DOCUMENTS

| | | |
|---|---|---|
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |

(56) References Cited

U.S. PATENT DOCUMENTS

| | | |
|---|---|---|
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0303520 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

* cited by examiner

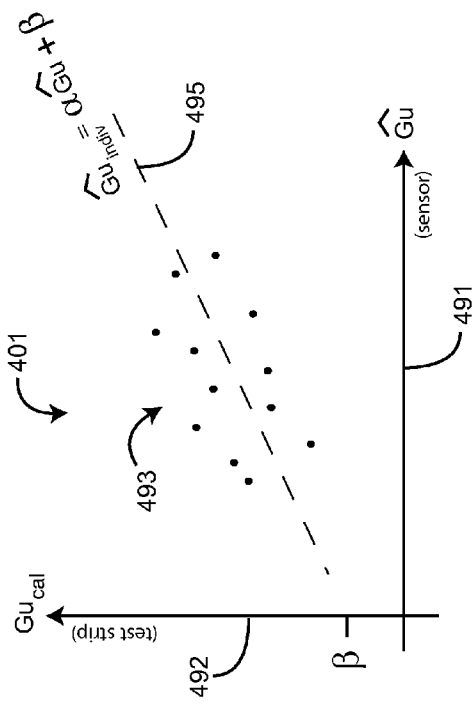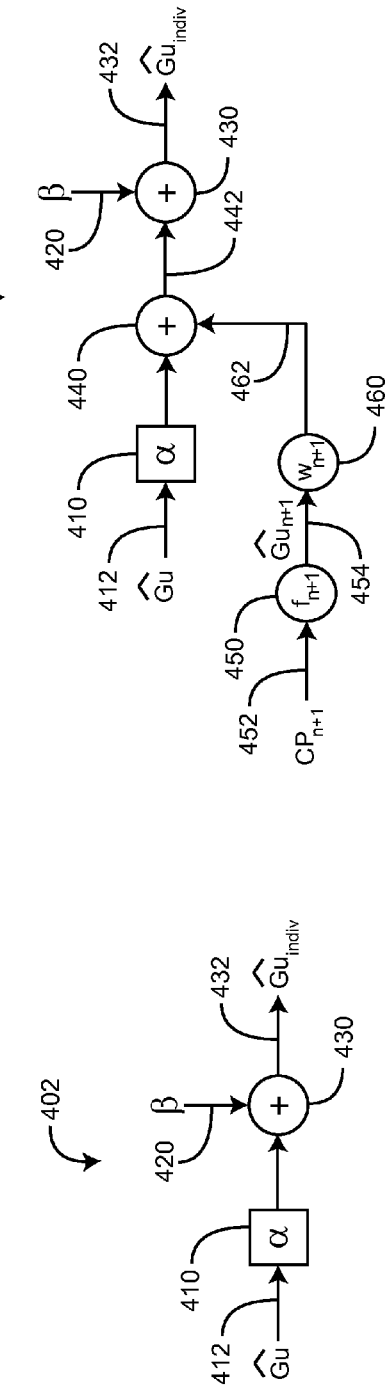
FIG. 4A
FIG. 4B
FIG. 4C

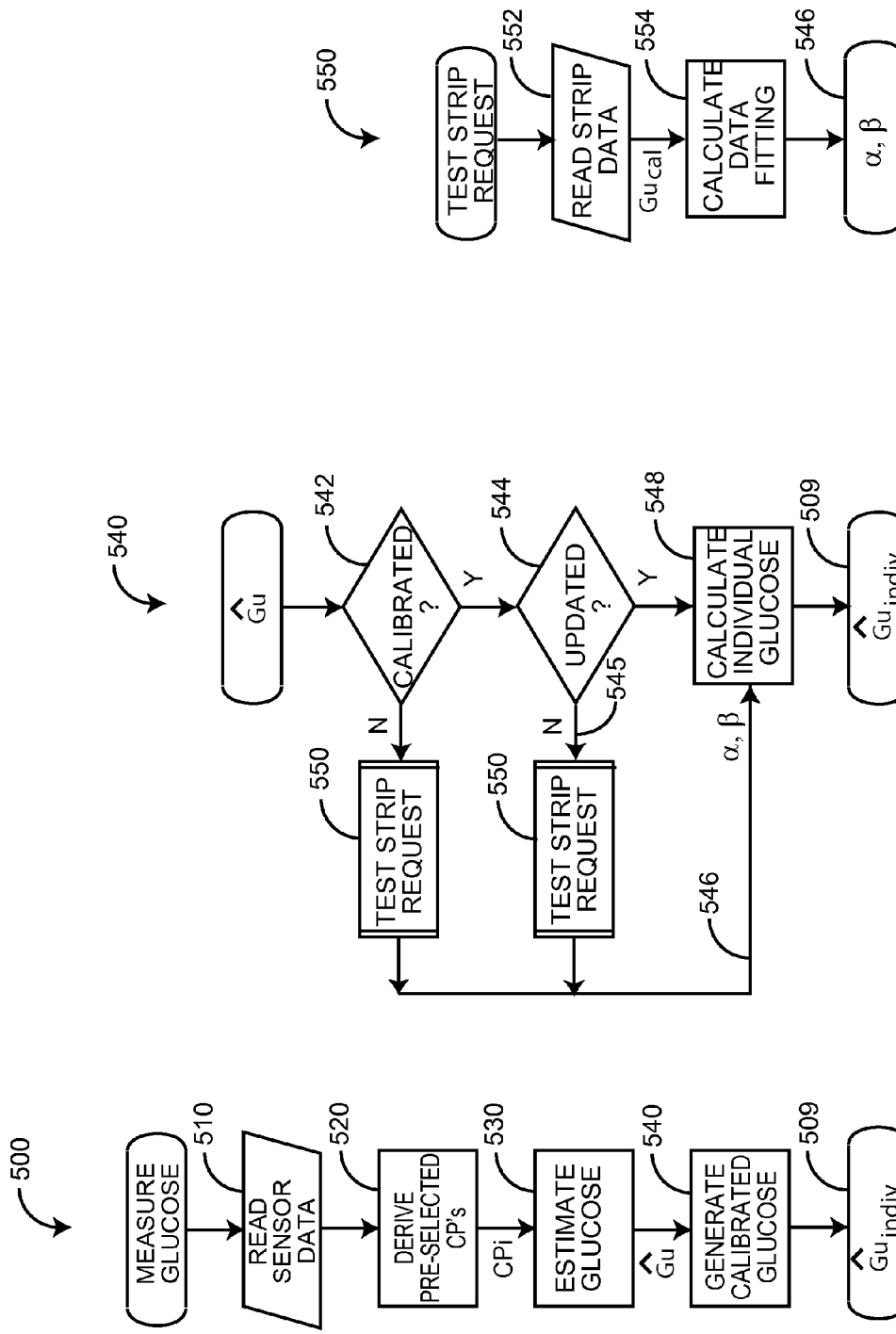

BLOOD GLUCOSE CALIBRATION SYSTEM

PRIORITY CLAIM AND REFERENCE TO RELATED APPLICATIONS

The present application claims priority benefit under 35 U.S.C. §119(e) to U.S. Provisional Patent Application Ser. No. 61/579,460, filed Dec. 22, 2011, titled Blood Glucose Calibration System, hereby incorporated in its entirety by reference herein.

BACKGROUND OF THE INVENTION

Medical device manufacturers are continually increasing the processing capabilities of patient monitors, specifically of patient monitors that process signals based on attenuation of light by patient tissue. In general, such patient monitoring systems include one or more optical sensors that irradiate tissue of a patient and one or more photodetectors that detect the radiation after attenuation thereof by the tissue. The sensor communicates the detected signal to a patient monitor, where the monitor often removes noise and preprocesses the signal. Advanced signal processors then perform time domain and/or frequency domain processing to determine measurements of blood constituents and other physiological parameters of the patient.

Manufacturers have advanced basic pulse oximeters that determine measurements for blood oxygen saturation ("SpO2"), pulse rate ("PR") and pethysmographic information, to read-through-motion oximeters, to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring Sp02, PR, perfusion index ("PI") and others. Masimo sensors include any of LNOP®, LNCS®, SofTouch™ and Blue™ adhesive or reusable sensors. Masimo oximetry monitors include any of Rad-8®, Rad-5®, Rad®-5v or SatShare® monitors.

Many innovations improving the measurement of blood constituents are described in at least U.S. Pat. Nos. 6,770,028; 6,658,276; 6,157,850; 6,002,952; 5,769,785 and 5,758,644, which are assigned to Masimo and are incorporated by reference herein. Corresponding low noise optical sensors are disclosed in at least U.S. Pat. Nos. 6,985,764; 6,088,607; 5,782,757 and 5,638,818, assigned to Masimo and hereby incorporated in their entirety by reference herein.

Masimo also manufactures more advanced co-oximeters including Masimo Rainbow® SET, which provides measurements in addition to Sp02, such as total hemoglobin (SpHb™), oxygen content (SpCO™), methemoglobin (SpMet®), carboxyhemoglobin (SpCO®) and PVI®. Advanced blood parameter sensors include Masimo Rainbow® adhesive, ReSposable™ and reusable sensors. Masimo's advanced blood parameter monitors include Masimo Radical-7™, Rad87™, and Rad57™ monitors as well as Pronto and Pronto-7 spot check monitors.

Innovations relating to these more advanced blood parameter measurement systems are described in at least U.S. Pat. Nos. 7,647,083; 7,729,733; U.S. Pat. Pub. Nos. 2006/0211925; and 2006/0238358, assigned to Cercacor Laboratories of Irvine, Calif. ("Cercacor") and hereby incorporated in their entirety by reference herein.

Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entirety by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entirety by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entirety by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated in its entirety by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad87™ and Rad57™ monitors, all available from Masimo. Advanced parameter measurement systems may also include acoustic monitoring such as acoustic respiration rate (RRa™) using a Rainbow Acoustic Sensor™ and Rad87™ monitor, available from Masimo. Such advanced pulse oximeters, low noise sensors and advanced parameter systems have gained rapid acceptance in a wide variety of medical applications, including surgical wards, intensive care and neonatal units, general wards, home care, physical training, and virtually all types of monitoring scenarios.

SUMMARY OF THE INVENTION

One aspect of a blood glucose calibration system has an optical sensor, a composite parameter generator, a glucose estimator, a strip meter and a glucose calibrator. The optical sensor illuminates a tissue site with multiple wavelength optical radiation and outputs multi-stream data responsive to the optical radiation after attenuation by blood flow within the tissue site. The composite parameter generator is responsive to the multi-stream data so as to calculate composite parameters indicative of constituents of the tissue site blood flow. The glucose estimator calculates a glucose estimate according to a weighted and scaled sum of the composite parameters. The strip meter intermittently reads a test strip exposed to blood drawn from an individual so as to generate a glucose calibration. The glucose calibrator generates an individually-calibrated glucose estimate from the glucose estimate and the glucose calibration.

Another aspect of a blood glucose calibration system utilizes a glucose calibration method to derive pre-selected composite parameters each responsive to a noninvasive multi-stream sensor in communications with an individual's blood flow. Blood glucose values are estimated over time from a combination of the composite parameters. Invasive blood glucose calibrations are measured over time from corresponding test strip readings. Individualized blood glucose values are calculated from a combination of the noninvasive blood glucose values and the invasive blood glucose calibrations. The invasive blood glucose calibrations intermittently update the individualized blood glucose values.

A further aspect of a blood glucose calibration system has a noninvasive sensor that attaches to a tissue site so as to generate multi-stream physiological data responsive to blood constituents. Composite parameters each in the form of a mathematical combination of invasive blood panel parameters are responsive to the multi-stream physiological data. A glucose estimate is derived from a weighted and scaled combination of the composite parameters. An individualized glucose estimate is derived from the glucose estimate and intermittent invasive test strip measurements of an individual.

An additional aspect of a blood glucose calibration system attaches a noninvasive sensor to a tissue site of a person so as to generate multi-stream physiological data responsive to that person's blood constituents. Composite parameters derived from a general population and each in the form of a mathematical combination of blood constituents are responsive to the multi-stream physiological data. A population-based, blood glucose estimate for that person is derived from a weighted and scaled combination of these composite parameters. An individualized blood glucose estimate is derived from the population-based blood glucose estimate and intermittent invasive test strip measurements from that person.

BRIEF DESCRIPTION OF THE DRAWINGS

FIG. 4A is a glucose calibration graph;

FIGS. 4B-C are flow diagrams of glucose calibrator embodiments;

FIGS. 5A-C are flowcharts of a glucose calibration method;

DETAILED DESCRIPTION OF THE PREFERRED EMBODIMENTS

Figure 1:
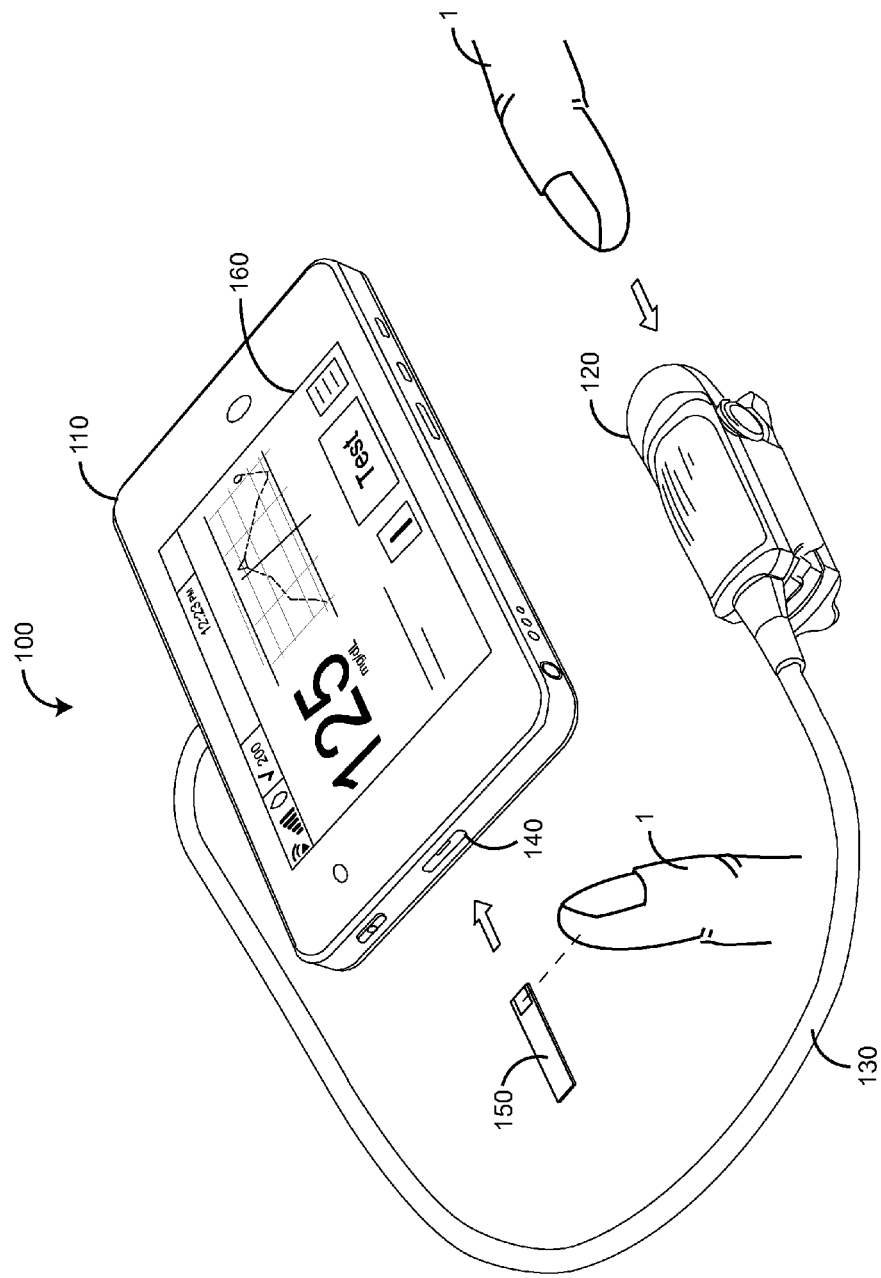
FIG. 1 is a perspective view of a blood glucose monitor utilizing a blood glucose calibration system.

FIG. 1 generally illustrates a blood glucose calibration system 100 that advantageously provides relatively frequent noninvasive measurements of blood glucose interspersed with relatively infrequent invasive measurements of blood glucose so as to manage individual blood glucose levels. The blood glucose calibration system 100 has a blood glucose monitor 110, an optical sensor 120, a sensor cable 130 electrically and mechanically interconnecting the monitor 110 and sensor 120 and a monitor-integrated test strip reader 710 (FIG. 7) that accepts test strips 150 via a test strip slot 140. In particular, the blood glucose calibration system 100 individually calibrates the noninvasive optical sensor 120 measurements with intermittent test strip measurements to advantageously provide the accuracy of individualized glucose test strip measurements at a much-reduced frequency of blood draws. Reduced blood draws is a substantial aid to persons who require frequent monitoring of blood glucose levels to manage diabetes and related diseases. In an embodiment, the monitor 110 has a handheld housing including an integrated touch screen 160 defining one or more input keys and providing a display of blood glucose levels among other features. An optical sensor is described in further detail with respect to FIG. 6, below. A blood glucose monitor is described in further detail with respect to FIG. 7, below. An optical sensor is also described in detail with respect to U.S. patent Ser. No. 13/646,659 titled Noninvasive Blood Analysis System, filed Oct. 5, 2012, assigned to Cercacor and incorporated in its entirety by reference herein. A blood glucose monitor is also described in detail with respect to U.S. patent Ser. No. 13/308,461 titled Handheld Processing Device Including Medical Applications for Minimally and Noninvasive Glucose Measurements, filed Nov. 30, 2011, assigned to Cercacor and incorporated in its entirety by reference herein. A blood glucose monitor and sensor are described in U.S. Ser. No. 13/473,477 titled Personal Health Device, filed May 16, 2012, assigned to Cercacor and incorporated in its entirety by reference herein.

Figure 2:
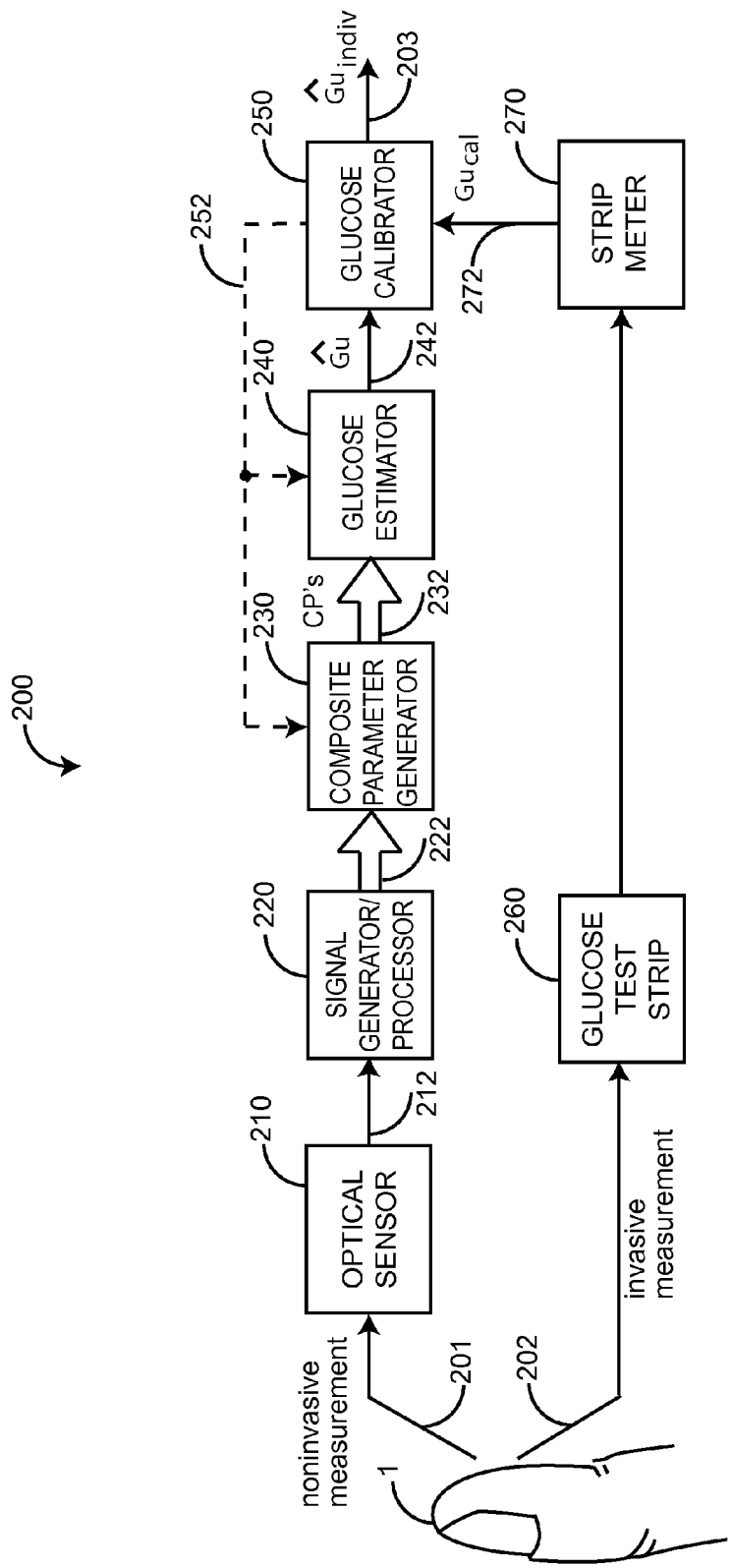
FIG. 2 is a general block diagram of a glucose calibration system.

FIG. 2 illustrates a blood glucose calibration system 200 embodiment that has a noninvasive measurement path 201 and an invasive measurement path 202. The noninvasive path 201 has an optical sensor 210, a signal generator/processor 220, a composite parameter generator 230, a glucose estimator 240 and a glucose calibrator 250. The optical sensor 210 attaches to and illuminates a tissue site 1 so as to generate sensor signals 212 responsive to blood constituents within the tissue site 1. The sensor signals 212 are input to the signal generator/processor 220, which outputs sensor data 222 to the composite parameter generator 230. The composite parameter generator 230 derives composite parameters CP's 232 indicative of one or more tissue site blood constituents. The glucose estimator 240 derives a blood glucose estimate $\widehat{Gu}$ 242 from one or more of the composite parameters CP's 232. The glucose calibrator 250 modifies the noninvasively-derived blood glucose estimate $\widehat{Gu}$ 242 in view of an invasively-derived glucose calibration $Gu_{cal}$ 272 so as to output an individually-calibrated blood glucose estimate $\widehat{Gu}_{indiv}$ 203.

As shown in FIG. 2, in an embodiment the sensor signals 212 incorporate optical sensor outputs responsive to multiple wavelengths of light after attenuation by pulsatile blood flow, active-pulsed blood flow and non-pulsatile fluids and tissue. Sensor signals 212 are also responsive to the relative phase differences of multiple wavelengths of light after attenuation by pulsatile blood flow. Further, sensor signals 212 are responsive to tissue site temperature, sensor temperature and the relative orientation of the tissue site. The signal generator/processor 220 generates hundreds of data streams 222 from the sensor signals 212. Composite parameters CP's 232, however, may only be responsive to, say, 40-70 of these data streams 222. The relationship between the data streams 222 and specific composite parameters $CP_i$ is determined by a correlation engine, which stores these relationships in a composite parameter look-up table. For each selected composite parameter $CP_i$, a relevant subset of the sensor data 222 is identified and the specific composite parameter $CP_i$ is calculated accordingly. An optical sensor and a composite parameter generator are described in detail with respect to U.S. patent application Ser. No. 13/646,659 titled Noninvasive Blood Analysis System, cited above.

Further shown in FIG. 2, the invasive measurement path 202 has a blood glucose test strip 260 measured by a strip meter 270. Although the blood glucose estimate $\widehat{Gu}$ 242, described above with respect to a noninvasive measurement path 201 is responsive to a particular patient, it is calibrated across a population of many individuals. Advantageously, the strip meter 270 provides an individualized measurement of blood glucose $Gu_{cal}$ 272, which is used to calibrate the blood glucose estimate $\widehat{Gu}$ 242 for a particular individual. A glucose test strip 260 is coated with a reagent that chemically reacts with the glucose in the blood. The strength of the reaction depends on glucose concentration. The strip meter 270 is responsive to the strength of the glucose-reagent reaction to determine glucose concentration. For example, the reaction strength may be proportional to a strip resistance electrically measured by the strip meter 270 and converted to a blood glucose measurement $Gu_{cal}$ 272. One of ordinary skill in art will appreciate that various glucose test strip and strip meter technologies may be used to derive a $Gu_{cal}$ measurement. In an embodiment, the glucose calibrator 250 may have feedback 252 that is responsive to $\widehat{Gu}$ or $Gu_{cal}$ or both so as to alter the composite parameters 232 chosen for the glucose estimate $\widehat{Gu}$ 242 and/or the weights associated with composite parameters in deriving the glucose estimate 242. A glucose calibration method is described in detail with respect to FIGS. 3-5, below.

Figure 3:
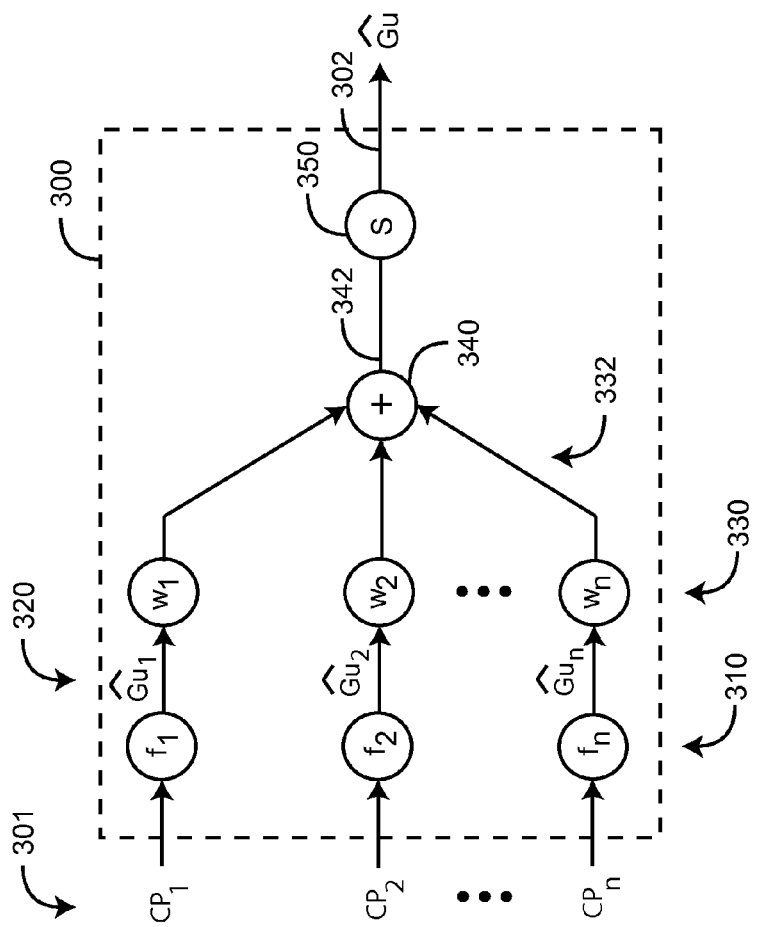
FIG. 3 is a general block diagram of a glucose estimator.

FIG. 3 illustrates a glucose estimator 300 embodiment having composite parameter inputs 301 and a glucose estimate output 302. The composite parameters are factored $f_i$ 310 into glucose estimates $\widehat{Gu}_i$ 320. The glucose estimates $\widehat{Gu}_i$ 320 are weighted 330, and the weighted estimates 332 are summed 340 to generate a weighted parameter sum 342. The weighted parameter sum 342 is scaled 350 to generate the glucose estimate $\widehat{Gu}$ 302 according to Eq. 1, where the scaling 350 is the inverse sum of the weights.

$$\widehat{Gu} = S \sum_{i=1}^{n} w_i \cdot \widehat{Gu}_i = \frac{\sum_{i=1}^{n} w_i \cdot \widehat{Gu}_i}{\sum_{i=1}^{n} w_i} \qquad \text{EQ. 1}$$

As shown in FIG. 3, in an embodiment the composite parameters 322 may be composed of one or more of the glucose composite parameters listed in Appendix A, attached hereto. The factors 310 are applied to the composite parameters 301 to generate factored glucose estimates $\widehat{Gu}_i$ 320 from the composite parameters. In an exemplar embodiment, the composite parameters are Gu/BUN, Gu*A1C and Gu, where BUN is blood urea nitrogen and A1C is glycated hemoglobin, each obtained from, say, an invasively derived blood panel. Then, the factors 310 are $f_1$=BUN; $f_2$=1/A1C; and $f_3$=1.

In an embodiment, the weights $w_i$ 330 are each 1 and the scaling S 350 is 1/n. However, some composite parameters may be better estimators of glucose than others. Accordingly, in other exemplar embodiments, each weight $w_i$ 330 is inversely proportional to the glucose measurement error $\sigma_i^2$ of its respective factored glucose estimate $\widehat{Gu}_i$ 320, and:

$$\widehat{Gu} = \frac{\sum_{i=1}^{n} \frac{1}{\sigma_i^2} \cdot \widehat{Gu}_i}{\sum_{i=1}^{n} \frac{1}{\sigma_i^2}} \qquad \text{EQ. 2}$$

In other embodiments, weights are determined by data fitting or long-term calibration methods, such as described with respect to FIGS. 4-5, below.

FIGS. 4A-C illustrate glucose calibrator embodiments for generating an individualized measurement of glucose $\widehat{Gu}_{indiv}$ from a noninvasively measured glucose estimate $\widehat{Gu}$. Shown in FIG. 4A is an exemplar scatter plot 401 of test strip measured glucose values $Gu_{cal}$ 492 versus corresponding sensor measured glucose estimates $\widehat{Gu}$ 491, shown as a set of n points 493. Overlaying the scatter plot 493 is a simple linear regression 495 that fits a straight line through the n points 493 such that the sum of squared residuals is minimized. In particular, the linear regression is $$\widehat{Gu}_{indiv} = \alpha \widehat{Gu} + \beta \qquad \text{EQ. 3}$$

where $\alpha$ and $\beta$ are the slope and y-intercept.

As shown in FIG. 4B, in a glucose calibrator embodiment 402, a gain 410 and offset 420 are applied to a glucose estimate $\widehat{Gu}$ 412 to yield an individualized glucose estimate $\widehat{Gu}_{indiv}$ 432 according to EQ. 3. The individualized glucose estimate advantageously converts a population-based non-invasive (sensor) glucose measurement to an individual-based sensor glucose measurement accordingly to a relatively small number of invasive (test strip) glucose measurements, as described above.

As shown in FIG. 4C, in another glucose calibrator embodiment 403, an additional composite parameter $CP_{n+1}$ 452 may be used to further refine the individualized glucose estimate $\widehat{Gu}_{indiv}$ 432 according to EQ. 4.

$$\widehat{Gu}_{indiv} = \alpha \widehat{Gu} + w_{n+1} \widehat{Gu}_{n+1} + \beta \qquad \text{EQ. 4}$$

One of ordinary skill in the art will recognize that multiple additional composite parameters $CP_{n+2}$, $CP_{n+3}$ . . . may be used to further refine the individualized glucose estimate $\widehat{Gu}_{indiv}$ 432. In other embodiments, an individualized glucose estimate $\widehat{Gu}_{indiv}$ 432 may be derived from a generalized data fitting of noninvasive glucose estimates $\widehat{Gu}$ to individual test strip measurements.

FIGS. 5A-C illustrate a glucose calibration method 500 embodiment that inputs optical sensor data 510 and outputs individualized glucose measurements $\widehat{Gu}_{indiv}$ 509. As shown in FIG. 5A, sensor data 510 is used to derive a preselected set of composite parameters CP's 520. In various embodiments, the composite parameters are selected on the basis of the highest correlation with invasively-measured glucose over a general population of interest; the highest correlation with invasively-measured glucose over a specific population matching a patient of interest; or the lowest error in the measurement of glucose, to name a few CP selection criteria. A glucose estimate 530 derives an uncalibrated glucose value $\widehat{Gu}$ from the composite parameter values $CP_i$. The derived glucose estimate $\widehat{Gu}$ assumes a tested individual's glucose corresponds to the average glucose across a population of individuals according to the measured CP's. Next, the population-based glucose estimate $\widehat{Gu}$ is refined by deriving an individually-calibrated glucose estimate $\widehat{Gu}_{indiv}$ 540.

As shown in FIG. 5B-C, glucose calibration 540 determines if glucose has been fully calibrated 542. If not, an individual test strip measurement is requested 550. A glucose meter reads the test strip 552 (FIG. 5C) so as to generate a glucose calibration value $Gu_{cal}$, as described with respect to FIG. 2, above. In an embodiment, the relationship between the (noninvasive) glucose estimate $\widehat{Gu}$ and the (invasive) test strip glucose value $Gu_{cal}$, is determined by a data fitting 554, such as a linear regression having a gain α and offset β, as described above. Multiple test strip calibration values $Gu_{cal}$ derived over a period of time may be required to determine the data fitting 554. An individual glucose value is calculated 548 from the data fitting 554 so as to output $\widehat{Gu}_{indiv}$ 509, as described with respect to FIGS. 4A-C, above.

Also shown in FIG. 5B, calibration may take multiple comparisons of noninvasive and invasive readings over a period of time. Once an individual relationship between invasive test strip-based glucose readings $Gu_{cal}$ and noninvasive multi-stream sensor-based values $\widehat{Gu}$ is established, a patient may rely on $\widehat{Gu}_{indiv}$ 509 for a longer period of time. This period may be pre-established or determined during the calibration phase. In an embodiment, this calibration or learning period establishes not only the data fitting relationship between noninvasive/invasive measurements but also the drift over time, i.e. the estimated period of validity between invasive updates 544. When the time period since the last update is exceeded 545, then another test strip measurement is requested 550.

Figure 6:
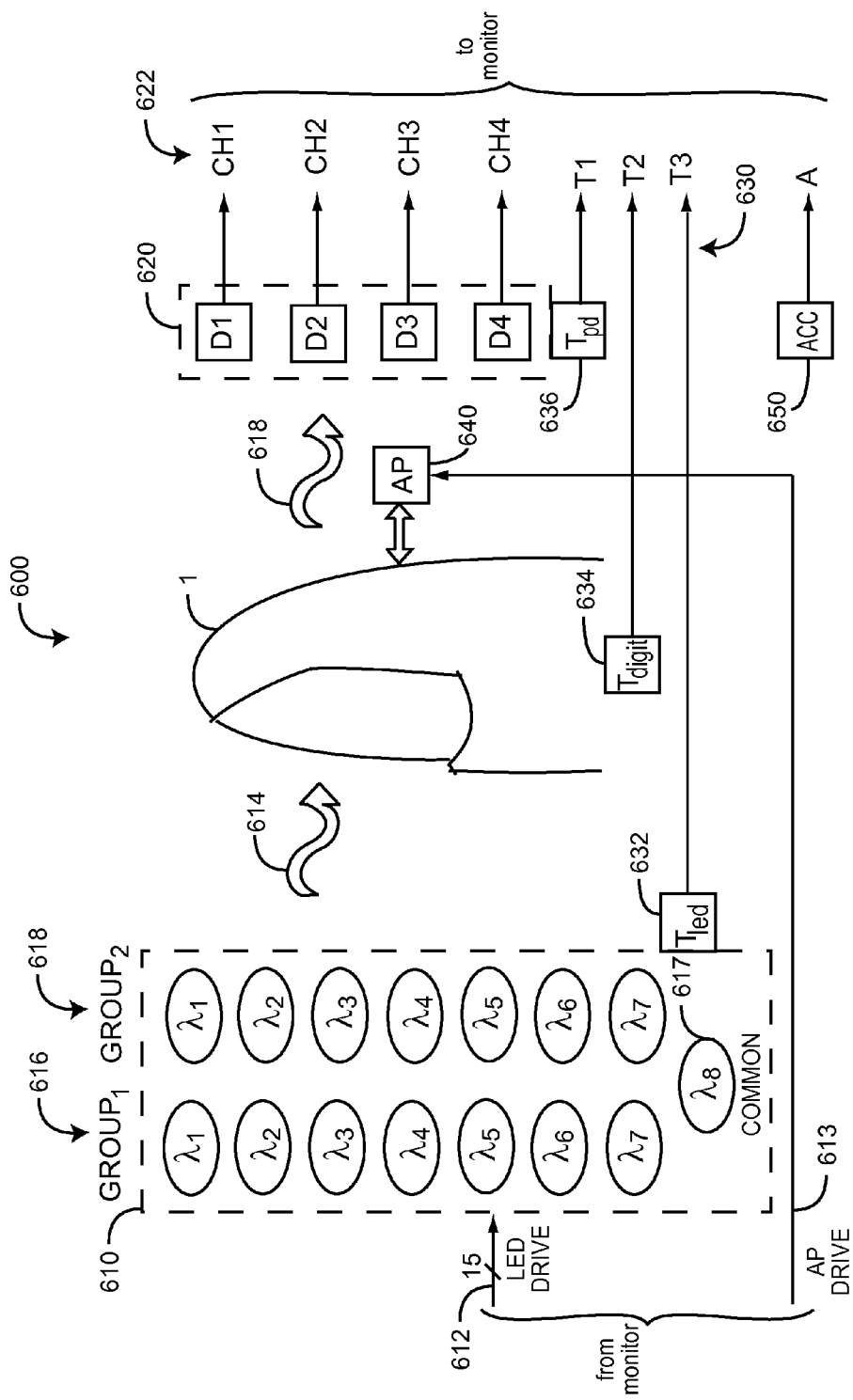
FIG. 6 is a detailed block diagram of a multi-stream sensor for noninvasive blood glucose monitoring.

FIG. 6 illustrates an optical sensor 600 for noninvasive blood glucose monitoring, as generally described with respect to FIGS. 1-2, above. The sensor 600 has LEDs (emitters) 610, detectors 620, temperature sensors 630, an active pulser 640 and an accelerometer 650. The LEDs 610 are individually activated by LED drives 612 so as illuminate a tissue site 1 with optical radiation 614. The detectors 620 receive attenuated optical radiation 618 after absorption, reflection and diffusion by the tissue site 1 and by pulsatile blood flow within the tissue site 1. The active pulser (AP) 640 has a motor that generates a mechanical "active pulse" in response to an AP drive signal 613. The motor has a "motor-on" state for starting the active (or artificial) pulse and a "motor-off" state for stopping the active pulse. Accordingly, the pulsatile blood flow may be arterial blood flow, AP blood flow, or both. The detectors 620 generate multiple channels 622 of plethysmograph and AP signals to a DSP 720 (FIG. 7) within a blood analysis monitor 700 (FIG. 7) for signal processing and analysis, as described in detail below.

As shown in FIG. 6, in a particular embodiment, the LEDs 610 are organized in two groups 616, 618 of seven LEDs each. The two groups also share a common LED 617. Hence, each group 616, 618 has eight LEDs, which are individually activated so as to emit eight wavelengths in sequence. In a particular embodiment, the temperature sensors include a $T_{led}$ sensor 632 responsive to the temperature of the LEDs 610, a $T_{digit}$ sensor 634 responsive to the temperature of the fingertip 1 and a $T_{pd}$ sensor 636 responsive to the temperature of the photodiode detectors 620. The accelerometer 650 indicates the sensor orientation and movement and is used by the signal processor in determining valid plethysmographs (pleths). An optical sensor is described in U.S. Ser. No. 13/473,477 titled Personal Health Device, cited above.

Figure 7:
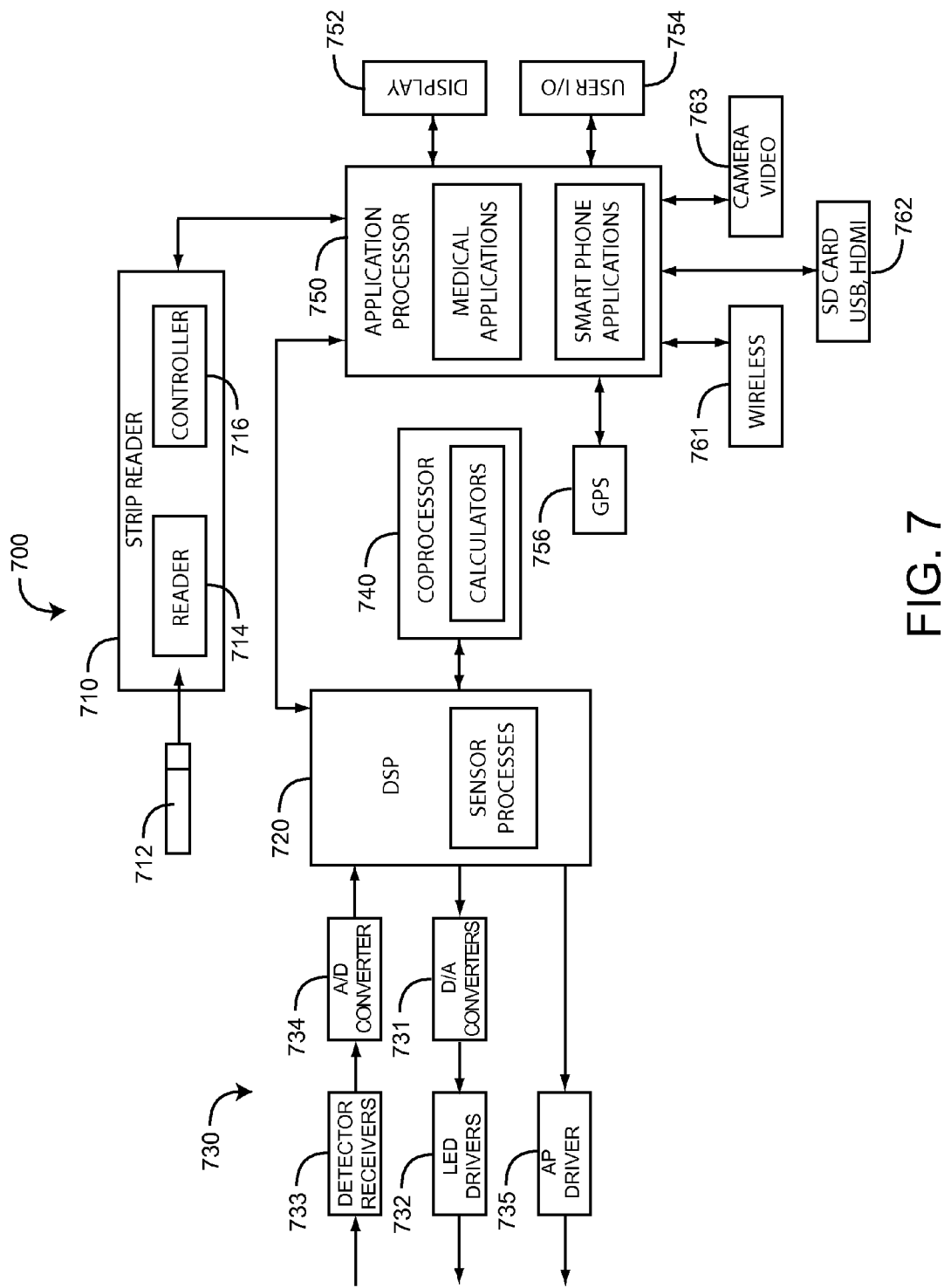
FIG. 7 is general block diagram of a blood glucose monitor.

FIG. 7 illustrates a blood glucose monitor 700, such as shown pictorially in FIG. 1, above. The monitor 700 has a plurality of processors, including a DSP 720 that performs sensor signal processing, a coprocessor 740 that assists the DSP 720 in intensive calculations, and an application processor 750 that executes medical and smart phone applications, including, for example, cell phone, Internet, entertainment, and productivity applications. A front end 730 having LED driverss 732, detector receivers 733, DACs 731, an ADC 734 and an active pulse (AP) driver 735 communicates with the sensor 600 (FIG. 6) to accomplish noninvasive sensor measurements. The DSP 720 additionally communicates with the applications processor 750 for display 752 and user I/O 754 functions. The applications processor 750 also communicates with the strip reader 710. In an embodiment, the strip reader 710 comprises a commercially available OEM strip reader. In an embodiment, the strip reader 710 includes a current detector or reader 714 and a controller 716 for determining from an inserted strip 712 minimally invasive glucose measurements. The reader 710 forwards calculated measurements to the applications processor 750, where, for example, medical applications use the data to present information to the user on the display 752.

Figure 8:
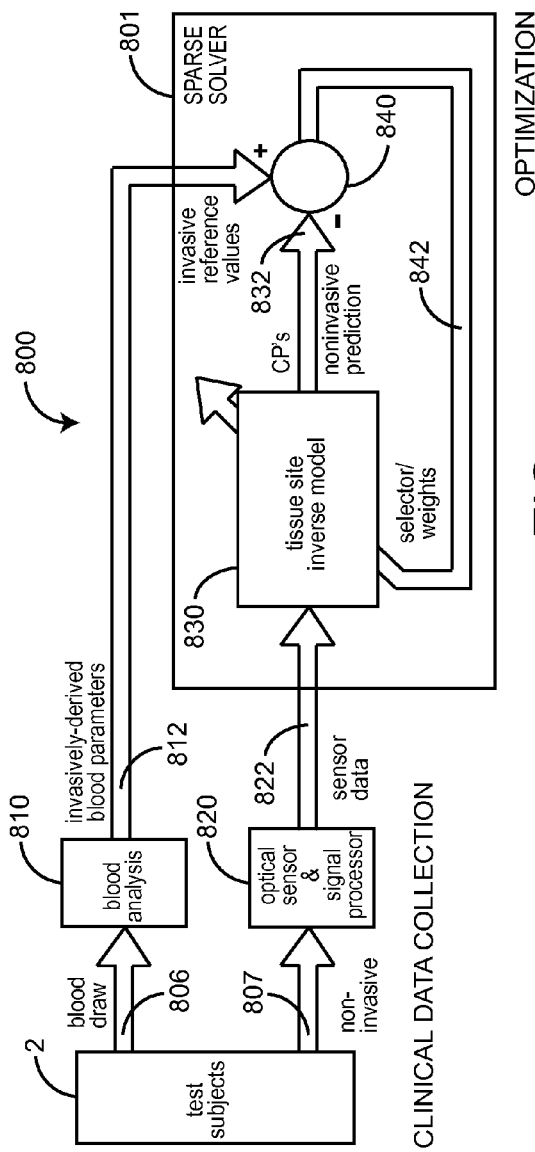
FIG. 8 is a general block diagram of a sparse solver for defining composite parameters.

FIG. 8 illustrates a correlation engine 800 for defining composite parameters 832. In particular, the composite parameters 832 correlate to the sensor data 822 described with respect to FIG. 10, below, where the composite blood parameters (CP) are of the forms:

$$CP=B_i;\ CP=B_i/B_j;\ CP=B_i+B_j;\ CP=B_i \cdot B_j/B_k;$$

$$CP=B_i/(B_j+B_k);\ CP=B_i/(B_j+B_k+B_l) \qquad \text{EQ. 5}$$

Of particular interest are glucose related composite parameters, such as listed and described in Appendix A, attached hereto. The correlation engine 800 has a clinical data collection portion and an optimization portion. Clinical data collection compares invasive blood draw measurements 806 from test subjects 2 to noninvasive sensor measurements 807 of the same test subjects 2. Optimization utilizes a sparse solver 801, which trains an inverse tissue site model 830 to predict composite parameters CPs 832 derived noninvasively from sensor data 822 within an acceptable error 842 of the invasively derived composite parameter 812.

As shown in FIG. 8, the clinical data collection derives an invasive blood panel 812 that generates a myriad of blood constituents ($B_i$) 812 such as blood urea nitrogen (BUN), high-density lipoprotein (HDL), low-density lipoprotein (LDL), total hemoglobin (THB), creatine (CRE) to name just a few. Data collection then assembles parameter combinations from the blood constituents so as to derive combinations parameters 832. The invasively-derived composite parameters 812 are then compared 840 to the predicted composite parameters 832 derived from the inverse tissue site model 830 so as to optimize the inverse model. Composite parameters that do not provide a high enough correlation are rejected. Appendix A, attached hereto, illustrates results obtained for approximately 60 sufficiently correlated composite parameters having glucose as a constituent.

Figure 9:
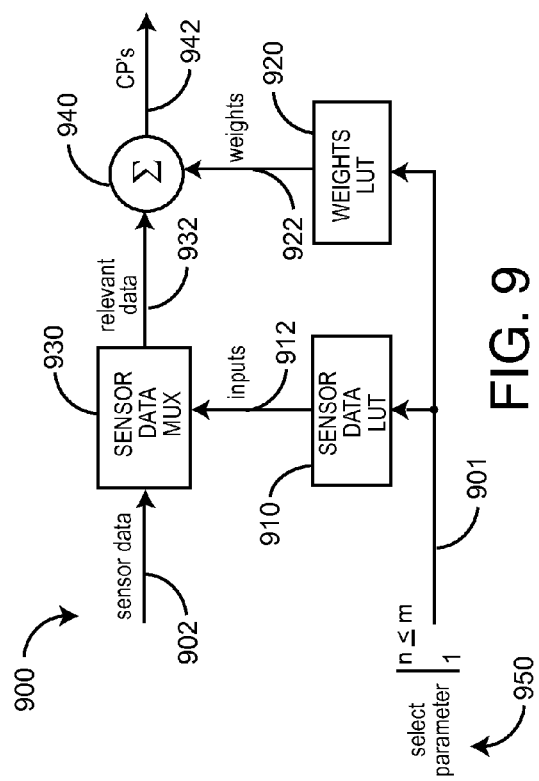
FIG. 9 is a general block diagram of a composite parameter generator for noninvasive blood glucose monitoring.

FIG. 9 illustrates a composite parameter generator 900 for noninvasive blood glucose monitoring having a sensor data 902 input and that advantageously generates a noninvasive blood analysis 942 output accordingly to selected blood parameters 950. Sensor data 902 includes ratios r, r-ap, tx and temp described with respect to FIG. 10, below. In an embodiment, sensor data 902 includes many data streams. However, each selected blood parameter may only be responsive to a small fraction of those data streams. The relationship between the sensor data 902 and a specific composite parameter 942 is determined by the sparse solver described above with respect to FIG. 8. In an embodiment, the relationships between a selected composite parameter 950 and the sensor data 902 that determines that selected parameter is stored in a sensor data look-up table 910. A sensor data multiplexer 930 outputs the relevant sensor data 932 for the selected parameter accordingly. The relevant data 932 for a particular parameter is weighted 922 and summed 940 so as to generate that composite parameter 942.

The particular weights 922 for a selected parameter 950 is stored in a weights look-up table 920. A range of composite parameters of interest 950 is selected 901 so as to calculate a particular blood constituent, such as blood glucose, as described above.

Figure 10:
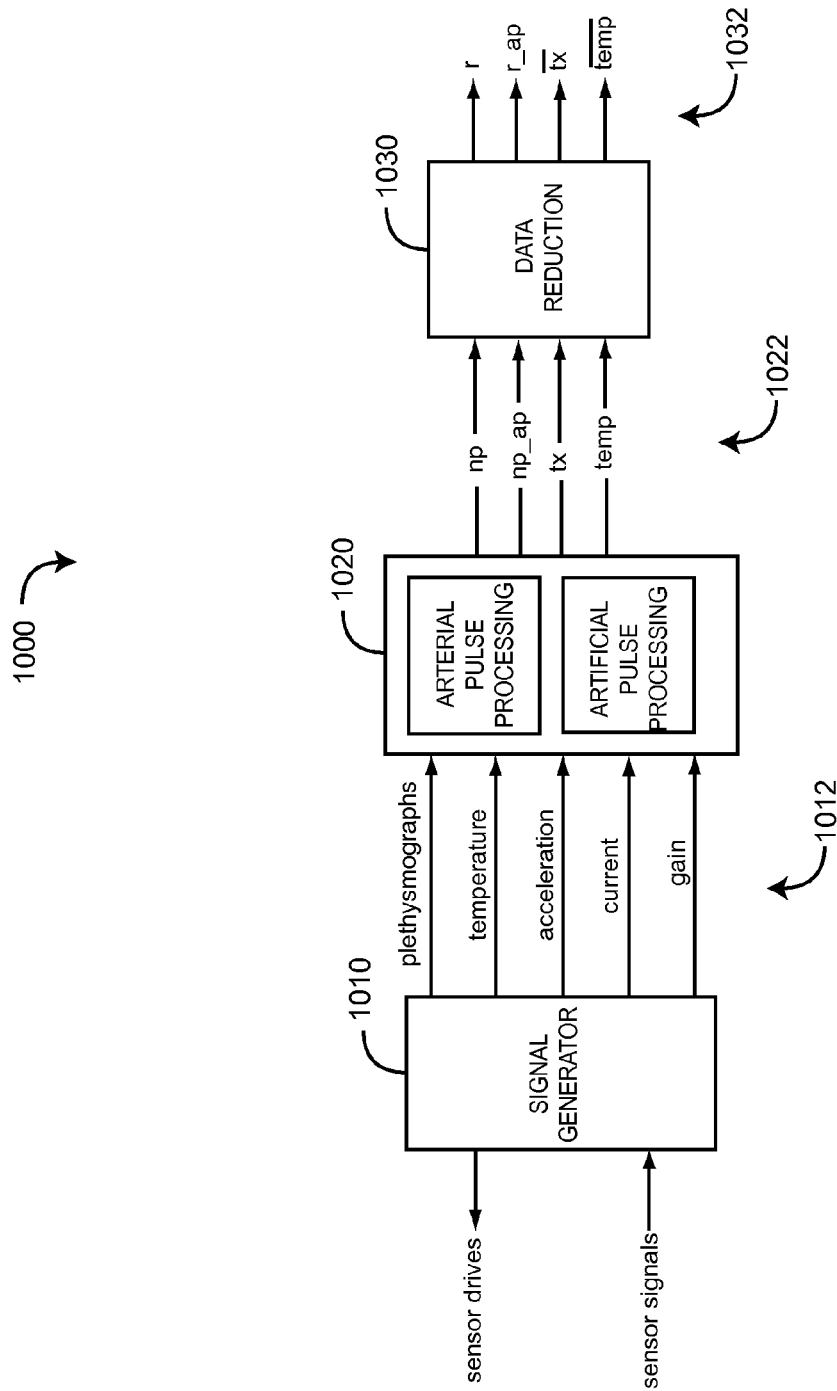
FIG. 10 is a general block diagram of optical sensor signal processing.

FIG. 10 illustrates optical sensor signal processing 1000, which has signal generator inputs 1012 including pleths, temperatures, currents and gains, along with sensor acceleration. Pulse processing 1020 normalizes and validates the pleths (np, np_ap) and generates transmittances (tx) from the currents and gains 1012. In an embodiment having two groups of 8 LEDs each and 4 detector channels, as described with respect to FIG. 6, above, the signal processor 1020 generates 32 (arterial) nps and 32 (artificial) np_ap's each, or 64 total normalized pleths for each of the two groups of LEDs. Data reduction 1030 reduces the normalized pleths to ratios (r, r_ap), reduces transmittances to averaged and trimmed transmittances ($\overline{tx}$) and reduces temperatures to averaged temperatures ($\overline{temp}$). These data reduction outputs 1032 provide the sensor data 822 (FIG. 8) for the spare solver 801 (FIG. 8) and sensor data 902 (FIG. 9) for the composite parameter generator 900.

A blood glucose calibration system has been disclosed in detail in connection with various embodiments. These embodiments are disclosed by way of examples only and are not to limit the scope of the claims that follow. One of ordinary skill in art will appreciate many variations and modifications.

APPENDIX A

GLUCOSE COMPOSITE PARAMETERS

| Parameter | Corr Training | Arms Training | Corr Testing | Arms Testing | Lower bound of range | Upper bound of range | Units |
|---|---|---|---|---|---|---|---|
| Gu/BUN | 59.48 | 4.67 | 59.22 | 4.73 | 3.250 | 11.000 | mg/dL/mg/dL |
| Gu * A1C | 62.24 | 660.55 | 59.07 | 684.93 | 247.00 | 704.00 | mg/dL * % |
| Gu * TRIG | 60.12 | 16171.41 | 58.85 | 16483.95 | 3510.00 | 16500.00 | mg/dL * mg/dL |
| Gu * VLDL | 60.83 | 3199.26 | 58.61 | 3314.53 | 325.00 | 3300.00 | mg/dL * mg/dL |
| Gu/TBIL | 60.37 | 116.86 | 57.82 | 119.33 | 46.429 | 1100.000 | mg/dL/mg/dL |
| Gu * TC/H | 61.45 | 266.07 | 57.51 | 269.44 | 84.50 | 550.00 | mg/dL * % |
| Gu * ALP | 60.37 | 4624.79 | 56.59 | 4806.85 | 2730.00 | 14080.00 | mg/dL * U/L |
| Gu * BUN | 59.45 | 979.38 | 56.45 | 1008.51 | 650.00 | 2200.00 | mg/dL * mg/dL |
| TBIL/Gu | 58.78 | 0.00 | 55.24 | 0.00 | 0.001 | 0.022 | mg/dL/mg/dL |
| BUN/Gu | 58.49 | 0.05 | 55.09 | 0.05 | 0.091 | 0.308 | mg/dL/mg/dL |
| Gu * LDL | 57.61 | 6782.19 | 55.02 | 7013.85 | 5200.00 | 14300.00 | mg/dL * mg/dL |
| Gu/HDL | 57.09 | 1.33 | 54.97 | 1.40 | 0.756 | 3.143 | mg/dL/mg/dL |
| Gu/CRE | 58.24 | 107.54 | 54.88 | 111.24 | 65.000 | 183.333 | mg/dL/mg/dL |
| Gu * CHOL | 57.75 | 11751.11 | 54.69 | 12450.89 | 7800.00 | 27500.00 | mg/dL * mg/dL |
| Gu/AST | 57.28 | 2.64 | 53.66 | 2.77 | 1.625 | 18.333 | mg/dL/U/L |
| Gu * AST | 56.20 | 1885.64 | 52.27 | 1927.72 | 390.00 | 4400.00 | mg/dL * U/L |
| Gu * HDL | 54.17 | 3511.27 | 51.73 | 3577.18 | 2275.00 | 9460.00 | mg/dL * mg/dL |
| Gu/ALT | 56.20 | 3.88 | 51.71 | 4.09 | 3.095 | 22.000 | mg/dL/U/L |
| HDL/Gu | 54.25 | 0.18 | 51.50 | 0.18 | 0.318 | 1.323 | mg/dL/mg/dL |
| Gu/TRIG | 54.77 | 0.84 | 51.24 | 0.87 | 0.433 | 2.037 | mg/dL/mg/dL |
| Gu * Ca | 53.87 | 516.72 | 51.20 | 538.61 | 552.50 | 1155.00 | mg/dL * mg/dL |
| Gu * TP | 53.80 | 406.86 | 51.16 | 421.83 | 390.00 | 924.00 | mg/dL * mg/dL |
| ALT/Gu | 57.81 | 0.09 | 51.11 | 0.09 | 0.045 | 0.323 | U/L/mg/dL |
| Gu * TCO2 | 54.36 | 1575.15 | 50.50 | 1634.06 | 1495.00 | 3080.00 | mg/dL * mmol/dL |
| Gu * ALT | 53.58 | 1471.54 | 50.25 | 1504.40 | 325.00 | 2310.00 | mg/dL * U/L |
| CRE/Gu | 54.80 | 0.00 | 50.03 | 0.00 | 0.005 | 0.015 | mg/dL/mg/dL |
| Gu/VLDL | 56.86 | 4.12 | 49.88 | 4.47 | 2.167 | 22.000 | mg/dL/mg/dL |
| Gu/ALB | 55.53 | 15.58 | 49.63 | 16.28 | 11.818 | 31.429 | mg/dL/mg/dL |
| Gu * K | 51.87 | 254.07 | 49.28 | 261.80 | 227.50 | 550.00 | mg/dL * mmol/dL |
| Gu/Cl | 52.41 | 0.58 | 49.07 | 0.59 | 0.613 | 1.122 | mg/dL/mmol/dL |
| Gu/ALP | 50.17 | 1.00 | 47.88 | 1.01 | 0.508 | 2.619 | mg/dL/U/L |
| Gu | 51.95 | 56.59 | 47.80 | 57.79 | 65 | 110 | mg/dL |
| Gu * ALB | 51.92 | 213.93 | 47.63 | 220.91 | 227.50 | 605.00 | mg/dL * mg/dL |
| VLDL/Gu | 51.94 | 0.10 | 47.37 | 0.10 | 0.045 | 0.462 | mg/dL/mg/dL |
| Gu * Cl | 50.89 | 5554.49 | 47.26 | 5654.26 | 6370.00 | 11660.00 | mg/dL * mmol/dL |
| TRIG/Gu | 52.55 | 0.52 | 47.21 | 0.52 | 0.491 | 2.308 | mg/dL/mg/dL |
| Gu * Na | 51.92 | 7252.49 | 46.89 | 7446.16 | 8840.00 | 15950.00 | mg/dL * mmol/dL |
| Gu * CRE | 49.60 | 42.81 | 46.85 | 42.87 | 39.00 | 110.00 | mg/dL * mg/dL |
| Gu/Na | 52.03 | 0.45 | 46.81 | 0.45 | 0.448 | 0.809 | mg/dL/mmol/dL |

APPENDIX A-continued

GLUCOSE COMPOSITE PARAMETERS

| Parameter | Corr Training | Arms Training | Corr Testing | Arms Testing | Lower bound of range | Upper bound of range | Units |
|---|---|---|---|---|---|---|---|
| Gu/TCO2 | 49.43 | 2.10 | 46.36 | 2.17 | 2.321 | 4.783 | mg/dL/mmol/dL |
| Gu/K | 49.95 | 12.98 | 46.33 | 13.46 | 13.000 | 31.429 | mg/dL/mmol/dL |
| Gu/Ca | 49.60 | 6.21 | 46.19 | 6.45 | 6.190 | 12.941 | mg/dL/mg/dL |
| Gu/TP | 49.80 | 8.11 | 46.11 | 8.31 | 7.738 | 18.333 | mg/dL/mg/dL |
| ALB/Gu | 49.68 | 0.01 | 46.04 | 0.01 | 0.032 | 0.085 | mg/dL/mg/dL |
| TC/H/Gu | 52.31 | 0.01 | 45.92 | 0.01 | 0.012 | 0.077 | %/mg/dL |
| Gu/TC/H | 49.80 | 20.86 | 45.19 | 21.31 | 13.000 | 84.615 | mg/dL/% |
| ALP/Gu | 48.40 | 0.20 | 44.89 | 0.21 | 0.382 | 1.969 | U/L/mg/dL |
| AST/Gu | 46.34 | 0.12 | 43.82 | 0.12 | 0.055 | 0.615 | U/L/mg/dL |
| LDL/Gu | 47.83 | 0.31 | 42.86 | 0.32 | 0.727 | 2.000 | mg/dL/mg/dL |
| Gu/CHOL | 47.48 | 0.38 | 42.72 | 0.39 | 0.260 | 0.917 | mg/dL/mg/dL |
| Gu/LDL | 46.13 | 0.98 | 41.56 | 0.99 | 0.500 | 1.375 | mg/dL/mg/dL |
| Cl/Gu | 47.81 | 0.32 | 41.29 | 0.33 | 0.891 | 1.631 | mmol/dL/mg/dL |
| Ca/Gu | 46.15 | 0.03 | 40.95 | 0.03 | 0.077 | 0.162 | mg/dL/mg/dL |
| CHOL/Gu | 46.66 | 0.51 | 40.81 | 0.53 | 1.091 | 3.846 | mg/dL/mg/dL |
| TP/Gu | 46.33 | 0.02 | 40.74 | 0.02 | 0.055 | 0.129 | mg/dL/mg/dL |
| Na/Gu | 47.01 | 0.42 | 40.49 | 0.43 | 1.236 | 2.231 | mmol/dL/mg/dL |
| TCO2/Gu | 43.36 | 0.09 | 38.90 | 0.09 | 0.209 | 0.431 | mmol/dL/mg/dL |
| K/Gu | 45.49 | 0.01 | 38.58 | 0.01 | 0.032 | 0.077 | mmol/dL/mg/dL |
| Gu * TBIL | 42.18 | 40.80 | 37.29 | 42.54 | 6.50 | 154.00 | mg/dL * mg/dL |
| Gu/A1C | 41.13 | 6.68 | 36.42 | 6.88 | 10.156 | 28.947 | mg/dL/% |
| A1C/Gu | 40.27 | 0.03 | 34.46 | 0.03 | 0.035 | 0.098 | %/mg/dL |

What is claimed is:

1. A blood glucose calibration system comprising:
 a noninvasive optical sensor configured to illuminate optical radiation and output sensor signals responsive to attenuation of the optical radiation from pulsatile blood flow in a tissue site;
 a composite parameter generator responsive to the sensor signals so as to calculate a plurality of composite parameters corresponding to blood glucose;
 a glucose estimator that calculates a plurality of uncalibrated blood glucose estimates according to the plurality of composite parameters;
 a strip meter that reads test strips exposed to blood drawn from the person so as to generate a plurality of glucose calibrations; and
 a glucose calibrator that generates a plurality of calibrated blood glucose estimates from the plurality of uncalibrated blood glucose estimates according to the glucose calibrations,
 wherein the plurality of composite parameters comprise at least one of Gu/X and Gu*X, where "Gu" represents blood glucose and "X" represents a non-glucose blood parameter.

2. The glucose calibration system according to claim 1 wherein the glucose calibrator comprises a linear relationship between the uncalibrated blood glucose estimates and the calibrated blood glucose estimates.

3. The glucose calibration system according to claim 2 wherein the glucose estimator comprises a weighted sum of a plurality of factored glucose estimates.

4. The glucose calibration system according to claim 3 wherein the factored glucose estimates each comprise one of the composite parameters with the corresponding non-glucose blood parameter factored out.

5. The glucose calibration system according to claim 4 further comprising a signal generator responsive to the optical sensor so as to generate normalized plethysmographs.

6. A glucose calibration method comprising:
 deriving one or more pre-selected composite parameters, each responsive to a noninvasive multi-stream sensor in communications with a person's blood flow;
 estimating a plurality of blood glucose values over time from a combination of the one or more pre-selected composite parameters;
 generating a plurality of invasive blood glucose calibrations over time from a corresponding plurality of test strip readings; and
 calculating a plurality of individualized blood glucose values from a combination of the noninvasive blood glucose values and the invasive blood glucose calibrations,
 the invasive blood glucose calibrations intermittently updating the individualized blood glucose values,
 wherein the one or more preselected composite parameters comprise at least one of Gu/X and Gu*X, where "Gu" represents blood glucose and "X" represents a non-glucose blood parameter.

7. A glucose calibration method according to claim 6 wherein the estimating blood glucose values comprises:
 factoring the composite parameters to generate glucose estimates;
 weighting the glucose estimates according to the effectiveness of the composite parameters for predicting glucose;
 summing the weighted composite parameters; and
 scaling the weighted sum of the composite parameters.

8. A glucose calibration method according to claim 7 wherein the generating a plurality of invasive blood glucose calibrations comprises data fitting.

9. A glucose calibration method according to claim 8 wherein the generating a plurality of invasive blood glucose calibrations comprises:
 applying a gain to a sensor glucose estimate;
 applying an offset to the sensor glucose estimate; and
 wherein the gain and offset are determined by multiple test strip measurements.

10. A glucose calibration method according to claim 8 further comprising:
 deriving an additional composite parameter to refine the glucose estimate.

11. A glucose calibration method according to claim 10 wherein the weights are inversely proportional to glucose measurement error.

12. A glucose calibration method according to claim 10 wherein:
- the weights are equal to 1; and
- the scaling is equal to 1/n.

13. A glucose calibration apparatus comprising:
- an optical sensor means for generating physiological data responsive to the person's blood constituents;
- a composite parameter generator means for generating composite parameters in the form of mathematical combinations of blood constituents based on the physiological data;
- a glucose estimator means for deriving noninvasive glucose estimate from a weighted and scaled combination of a composite parameters subset of the composite parameters; and
- a glucose calibrator means for calibrating the noninvasive glucose estimate based on an invasive test strip measurement of the person,
- wherein the composite parameters comprise at least one of Gu/X and Gu*X, where "Gu" represents blood glucose and "X" represents a non-glucose blood parameter.

14. The glucose calibration apparatus according to claim 13 wherein the composite parameter generator means comprises:
- a selection means for identifying relevant data from the physiological data according to a selected one of the composite parameters; and
- a weight means for generating specified weights corresponding to the selected one of the composite parameters; and
- a weighted sum means for calculating the selected one of the composite parameters from the summation of the specified weights multiplied by the relevant data.

15. The glucose calibration apparatus according to claim 14 wherein the glucose estimator means comprises:
- a factor for generating a plurality of factored glucose estimates, and
- the factored glucose estimates weighted and scaled to generate the noninvasive glucose estimate.

16. The glucose calibration apparatus according to claim 15 wherein the glucose calibrator means comprises an individualized glucose estimate means for relating the noninvasive glucose measurement and the invasive test strip measurement.

* * * * *